(12) United States Patent
Do (10) Patent No.: US 12,408,818 B2
(45) Date of Patent: Sep. 9, 2025

(54) ENDOSCOPE COMPRISING A FLEXIBLE INSERTION TUBE AND A BENDING PORTION

(71) Applicant: HOYA CORPORATION, Tokyo (JP)

(72) Inventor: Anh Minh Do, Munich (DE)

(73) Assignee: HOYA CORPORATION, Tokyo (JP)

( * ) Notice: Subject to any disclaimer, the term of this patent is extended or adjusted under 35 U.S.C. 154(b) by 343 days.

(21) Appl. No.: 18/030,542

(22) PCT Filed: Sep. 22, 2021

(86) PCT No.: PCT/IB2021/058622
§ 371 (c)(1),
(2) Date: Apr. 6, 2023

(87) PCT Pub. No.: WO2022/074491
PCT Pub. Date: Apr. 14, 2022

(65) Prior Publication Data
US 2023/0371787 A1  Nov. 23, 2023

(30) Foreign Application Priority Data

Oct. 7, 2020  (DE) ...................... 10 2020 126 238.8

(51) Int. Cl.
*A61B 1/00* (2006.01)
*A61B 1/005* (2006.01)

(52) U.S. Cl.
CPC ...... *A61B 1/00078* (2013.01); *A61B 1/00098* (2013.01); *A61B 1/0055* (2013.01); *A61B 1/0057* (2013.01)

(58) Field of Classification Search
CPC ............ A61B 1/00078; A61B 1/00098; A61B 1/0055; A61B 1/0057
(Continued)

(56) References Cited

U.S. PATENT DOCUMENTS 4,807,598 A * 2/1989 Hasegawa .......... A61B 1/00071
600/153
5,002,041 A * 3/1991 Chikama ........... A61M 25/0138
600/146
(Continued)

FOREIGN PATENT DOCUMENTS

EP  0422842 A2  4/1991
EP  1690564 A1  8/2006
(Continued)

OTHER PUBLICATIONS

Notice of Reasons for Refusal issued in Japanese Patent Application No. PCT/IB2021/058622, dated Dec. 5, 2023, together with an English translation.
(Continued)

*Primary Examiner* — Aaron B Fairchild
(74) *Attorney, Agent, or Firm* — GREENBLUM & BERNSTEIN, P.L.C.

(57) ABSTRACT

An endoscope includes a flexible insertion tube and a bending portion controllable from a proximal side and being distally connected to the insertion tube. The bending portion includes a sleeve in which at least one pull rope runs for a pivoting movement of the bending portion, wherein the at least one pull rope is anchored to the distal end of the bending portion. A separating element dividing the cross-section of the sleeve into at least two separate chambers is arranged in the longitudinal direction of the sleeve. In one of the at least two chambers separated by the separating element, a pull rope of the at least one pull rope is arranged in the longitudinal direction of the sleeve for pivoting movement of the bending portion.

13 Claims, 7 Drawing Sheets

(58) Field of Classification Search
USPC .......................................................... 600/140
See application file for complete search history.

(56) References Cited

U.S. PATENT DOCUMENTS

| | | | |
|---|---|---|---|
| 5,106,381 A | 4/1992 | Chikama | |
| 6,409,658 B1 * | 6/2002 | Mitsumori | A61B 1/00188 600/130 |
| 10,702,134 B2 | 7/2020 | Do et al. | |
| 2002/0019582 A1 * | 2/2002 | Takase | A61B 1/125 600/140 |
| 2006/0184106 A1 | 8/2006 | McDaniel et al. | |
| 2007/0250038 A1 * | 10/2007 | Boulais | A61M 25/0026 604/523 |
| 2008/0269556 A1 * | 10/2008 | Jagasia | A61B 1/00098 600/118 |
| 2011/0218492 A1 | 9/2011 | McDaniel et al. | |
| 2020/0222666 A1 * | 7/2020 | Chan | A61B 34/20 |
| 2022/0022732 A1 | 1/2022 | Do | |

FOREIGN PATENT DOCUMENTS

| | | |
|---|---|---|
| JP | S48-31667 Y | 9/1973 |
| JP | S63-252128 A | 10/1988 |
| JP | H03-128026 A | 5/1991 |
| JP | H03-58402 U | 6/1991 |
| JP | H07-163514 A | 6/1995 |
| JP | 2017-205436 A | 11/2017 |

OTHER PUBLICATIONS

U.S. Appl. No. 18/030,402 to Anh Minh Do et al., which was filed Apr. 5, 2023.
International Search Report issued in International Bureau of WIPO Patent Application No. PCT/IB2021/058622, dated Nov. 15, 2021.
First Office Action issued in Chinese Patent Application No. 202180068779.9, dated Apr. 24, 2025, together with an English translation.

* cited by examiner

ENDOSCOPE COMPRISING A FLEXIBLE INSERTION TUBE AND A BENDING PORTION

The present invention relates to an endoscope comprising a flexible insertion tube and a bending portion controllable from a proximal side, the bending portion being distally connected to the insertion tube.

An endoscope of this type can be built with a very small diameter so as to examine also small openings of the body, for example.

Usually, the diameter of the bending portion is equal to or slightly different from the diameter of the insertion tube of the endoscope. In the case of endoscopes having a thin insertion tube, the bending portion is appropriately thin.

However, a thin bending portion frequently has no sufficient interior for the complex constructional designs required for a conventional bending portion. The bending portion of the endoscope can be controlled by the user. For this purpose, the bending portion is controlled, i.e., deflected, by the user from the proximal side of the endoscope.

Accordingly, from prior art various basic designs of the bending portion are known, such as a bending portion of articulated members made from metal or a bending portion made from articulated plastic elements.

In the bending portion of articulated members made from metal, the bending portion consists of a number of complexly shaped metal rings each being connected by a freely movable connection of annular joints. Said annular joints include hinge pins offset against their respective adjacent annular joint by 90 or, resp., 180 degrees. The bending portion can pivot upwards and downwards via a number of pivot points. Eyelets are arranged in plural rows at the annular joints on the inside of the deflectable portion. Said eyelets serve as a guide for pull ropes anchored to the distal end of the deflectable portion. The bending or deflecting movement of the deflectable portion is carried out by the pull ropes being pulled from the proximal side.

Said complex construction requires an appropriate interior inside the bending portion. If the bending portion is very thin, usually there is not sufficient interior space available.

In the bending portion of articulated plastic elements, plastic elements produced by injection molding are interconnected and pivotable relative to each other via hinges. Although a bending portion of articulated plastic elements shows a very simple construction, it offers even less interior space than the bending portion of articulated members made from metal. This is due to the fact that the partitions of a plastic member require a particular thickness to ensure sufficient stability and, resp., strength. In addition, also in this case eyelets require much space.

Thus, it is an object of the invention to provide an endoscope comprising a flexible insertion tube and a bending portion in which the bending portion makes available sufficient space in the interior. Furthermore, the bending portion of the endoscope is intended to offer satisfactory functionality.

This object is achieved by an endoscope comprising the features of claim 1. Advantageous developments are the subject matter of the dependent claims.

In the invention, an endoscope has a flexible insertion tube and a bending portion controllable from a proximal side, the bending portion being distally connected to the insertion tube, wherein the bending portion has a sleeve with at least one pull rope extending therein for a pivoting movement of the bending portion, the at least one pull rope being anchored to the distal end of the bending portion. In the longitudinal direction of the sleeve, a separating element is arranged for dividing the cross-section of the sleeve into two separate chambers. In one of the two chambers separated by the separating element, a pull rope of the at least one pull rope is arranged in the longitudinal direction of the sleeve for a pivoting movement of the bending portion.

The bending portion can easily be divided by the separating element into pull rope ducts extending in the longitudinal direction and being delimited to the radial side. In this way, an endoscope having a bending portion can be provided in a simple and cost-efficient manner. The simple design enables a particularly small construction size, as the principle of dividing the bending portion by the separating element into separate chambers can be applied to any construction size and, particularly, to very small endoscope diameters.

At least one pull rope is arranged in a chamber in this case. With this minimalistic structure already, the bending portion can be pivoted in a well-directed manner by pulling the one pull rope. The return movement of the bending portion after being deflected is caused by relieving the previously pulled pull rope.

In each of the two chambers separated by the separating element, a pull rope of the at least one pull rope may be arranged in the longitudinal direction of the sleeve for a pivoting movement of the bending portion. In this case, with two chambers separated by the separating element, a pull rope is provided in each chamber. Each of the pull ropes is guided in a separate chamber and, thus, in a separate pull rope passage without being impaired by the other pull rope.

The separating element may be arranged in the sleeve so that the separating element divides the cross-section of the sleeve into two separate chambers of equal size. Thus, in practice, the smallest dimension possible for the bending portion can be used.

The separating element may be anchored, at its proximal side, to the distal end region of the insertion tube. The separating element may be anchored, at its proximal side, to the distal end portion of the insertion tube such that its length protruding toward the distal side is predefined. Hence, anchoring can be realized to be safe and reliable but also to be easy and require little effort.

The insertion tube may include an outer cover and, beneath the outer cover, an elastic wire mesh, the proximal side of the separating element being anchored to the distal end region of the wire mesh. The wire mesh incorporated in the insertion tube gives firm support to the proximal side of the separating element.

The proximal side of the separating element may be inserted into or else welded to or glued into the distal end region of the wire mesh.

The sleeve of the bending portion may have an outer diameter of 3 mm or less. In the case of an even smaller design, the sleeve of the bending portion may even have an outer diameter of 1 mm or less. Thus, the endoscope is suitable for particularly small cavities which previously could hardly be examined by a flexible endoscope having a bending portion.

The separating element may be manufactured from spring steel, stainless steel or a flexible plastic material. The material of the separating element imparts flexibility. However, the separating element is neither compressible nor expandable.

The separating element may be made from various materials having different bending properties. Accordingly, in the separating element the various materials may be arranged so that they ensure a preferred bending direction of the separating element. For example, the separating element may be a metal plate with an upper surface and a lower surface being coated with rubber or plastic. The metal plate then is bendable toward the respective coating side.

The sleeve of the bending portion may include a spring element. In this way, both flexibility and the necessary stiffness can be imparted to the sleeve and, thus, to the bending portion. In addition, the bending portion can be configured to be twist-proof (torsion-resistant).

The spring element can be embedded in the sleeve of the bending portion. The material of the sleeve may be plastic or rubber. Thus, the sleeve equipped with the spring element is easy to manufacture. For example, the material of the sleeve may be injection-molded or extruded around the spring element.

The cross-section of the separating element may be configured such that the cross-section of the separating element is wider in a first direction and is narrower in a second direction that is perpendicular to the first direction. The cross-section of the separating element may have a rectangular, oval, elliptic or race-track shape (a so-called stadium shape). Hence, one side of the separating element is longer than the other side. The separating element bends around the thinner side. In this way, the bending direction is predetermined when pulling the pull rope. The separating element cannot be bent in the direction of the wider side of the cross-section.

The endoscope may be a flexible endoscope.

The afore-explained aspects of the present invention can be combined as appropriate.

BRIEF DESCRIPTION OF THE DRAWING

FIGS. 4A-4C show how the flexible plate of the first embodiment is inserted in an insertion tube. In particular.

In the following, the present invention is described in detail with reference to the drawings on the basis of embodiments. The representations in the drawings are not necessarily true-to-scale, but are sometimes shown distorted for reasons of better clarity.

First Embodiment

Below, a first embodiment of the present invention is described with reference to FIGS. 1 to 5.

Figure 1:
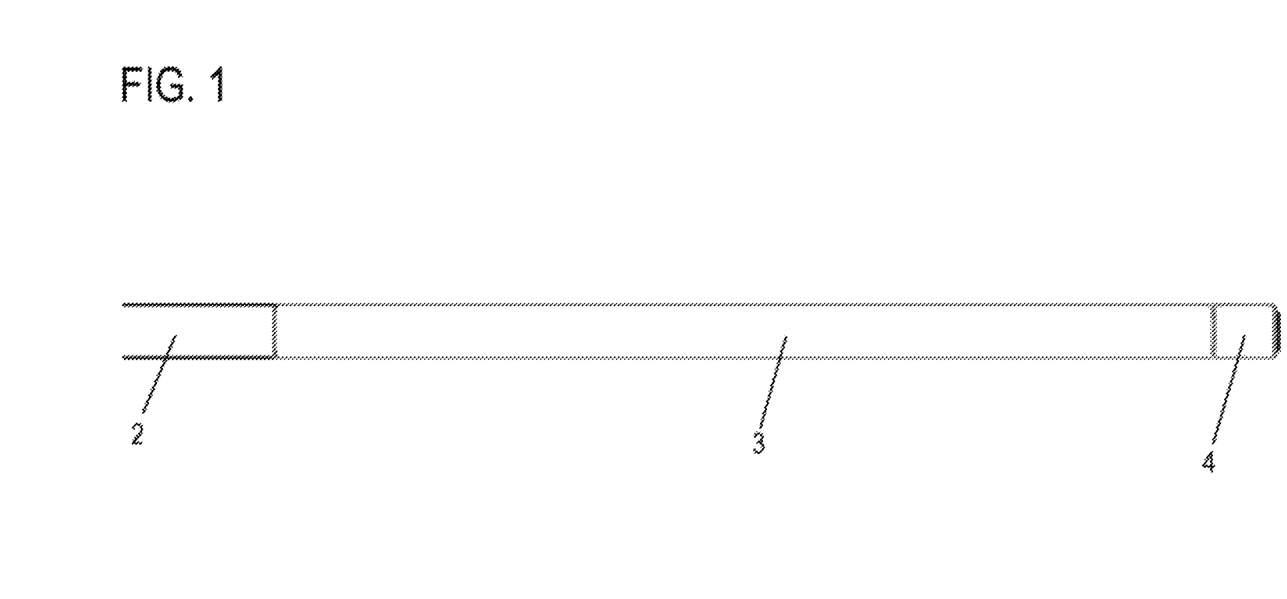
FIG. 1 shows a schematic side view of a distal region of an endoscope according to the invention.

An endoscope 1 according to the invention includes an insertion tube 2, a bending portion 3 and a distal end 4 on the distal side of a control member (not shown).

FIG. 1 illustrates a schematic side view of the distal region of the endoscope 1 according to the invention. On the distal side of the insertion tube 2, the bending portion 3 is disposed. On the distal side of the bending portion 3, the distal end 4 is disposed.

Insertion Tube 2

The insertion tube 2 is elastic and serves for being inserted, with the distal end 4 ahead, into a patient for the purpose of examination. The insertion tube 2 is bendable so that it is capable of following the bent openings of the body into which it is inserted. The insertion tube 2 is also sufficiently stiff and torsion-resistant so that it can be pushed forward past bends of the body openings. The insertion tube 2 includes a cover 21 on the outside and a wire mesh 22 preferably on the inside of the cover 21. The cover 21 protects the interior of the insertion tube 2. The wire mesh 22 imparts the required flexibility, stiffness and torsion resistance to the insertion tube 2.

Bending Portion 3

Figure 2:
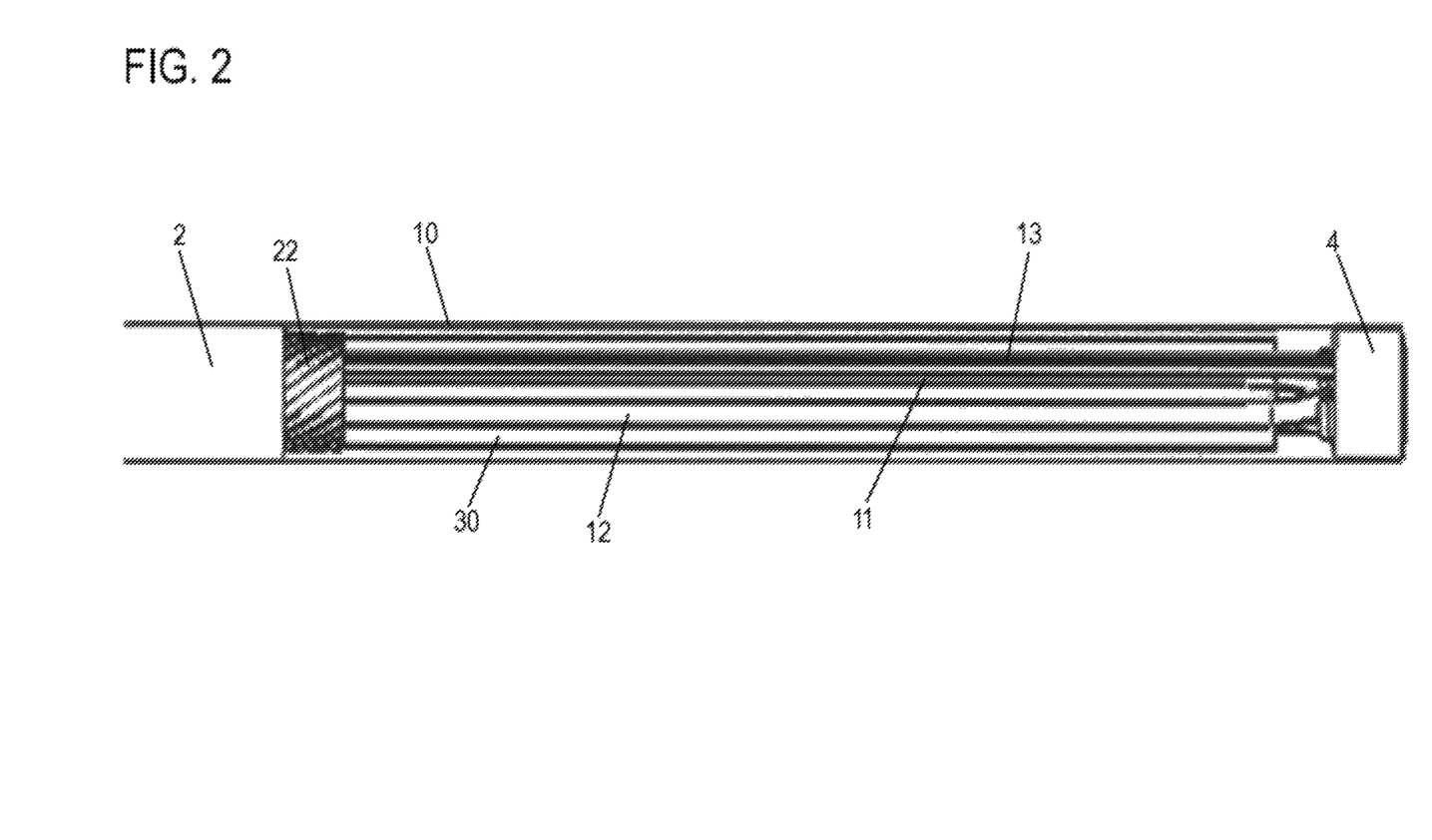
FIG. 2 shows a schematic side view of the interior of the bending portion in a first embodiment.

The bending portion 3 is located at the distal end of the insertion tube 2. The longitudinal direction of the bending portion 3 corresponds to the extension direction of the endoscope 1. The bending portion 3 is pivotable relative to the insertion tube 2. In order to realize the pivotability, pull ropes 11 fastened to the distal end 4 are guided in the bending portion 3. In the embodiment, two pull ropes 11 are provided. Pulling a pull rope 11 in the proximal direction causes the distance between the distal end of the insertion tube 2 and the distal end 4 at the radial side of the bending portion 3 where the pulled rope 11 is located to be reduced.

In the bending portion 3, an elastic sleeve 10 extends from the distal end of the insertion tube 2 to the distal end 4. The elastic sleeve 10 can be regarded as being a continuation of the cover 21 of the insertion tube 2 in the distal direction.

Separating Element 30

Figure 3:
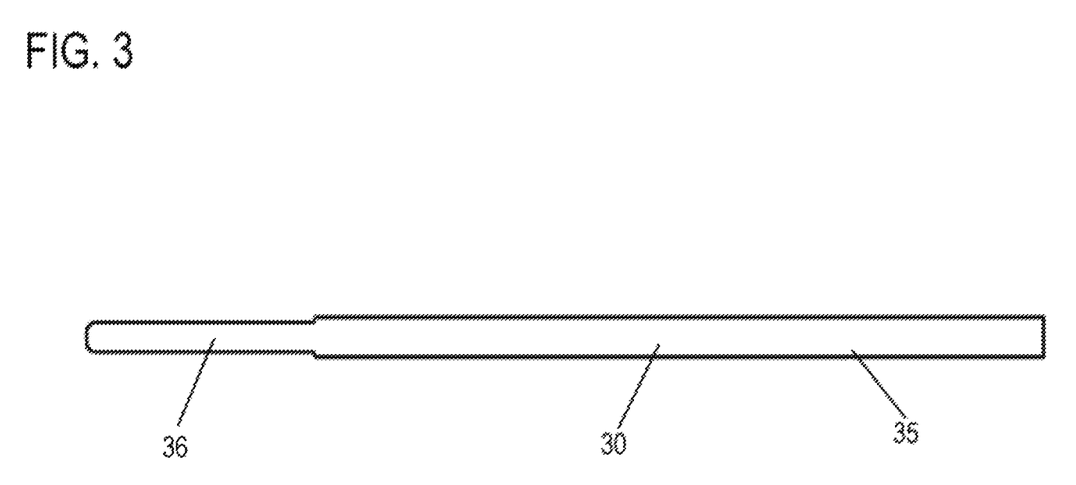
FIG. 3 shows a schematic top view onto a flexible plate of the first embodiment.

In the bending portion 3, a flat flexible plate 30 serving as a bendable plate is arranged as separating element. FIG. 3 illustrates an example of the flexible plate 30. In the top view, the flexible plate 30 takes the shape of an elongate rectangle. Moreover, the cross-section of the flexible plate 30 is in the form of a rectangle. In the top view of FIG. 3, the flexible plate 30 is bendable toward the viewer and away from the viewer.

The flexible plate 30 has a narrower proximal portion 36 and a wider distal portion 35. The proximal portion 36 has a shorter width than the distal portion 35.

Figure 4A:
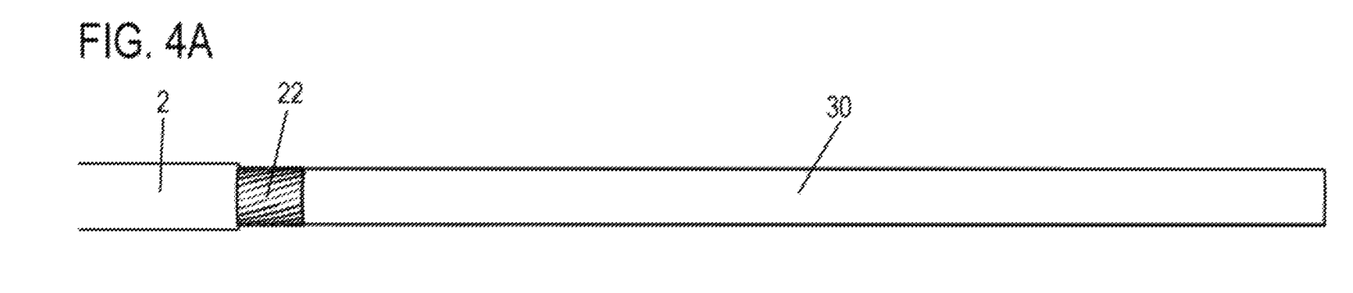
FIG. 4A shows a schematic top view.
Figure 4B:
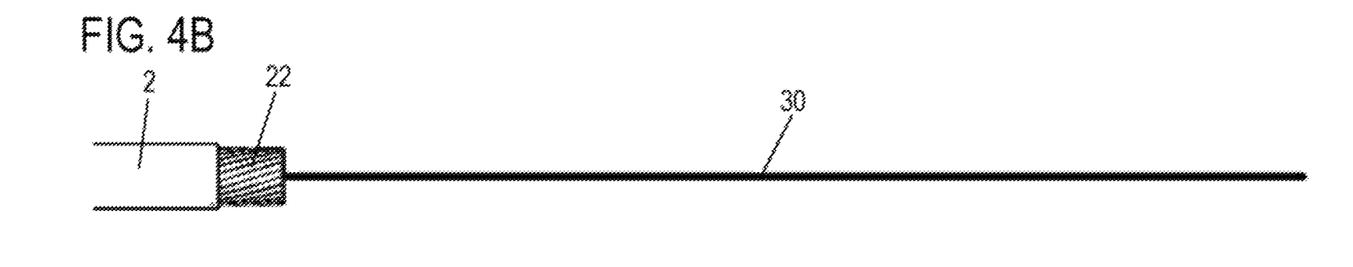
FIG. 4B shows a schematic side view and FIG. 4C shows a schematic perspective view.
Figure 4C:
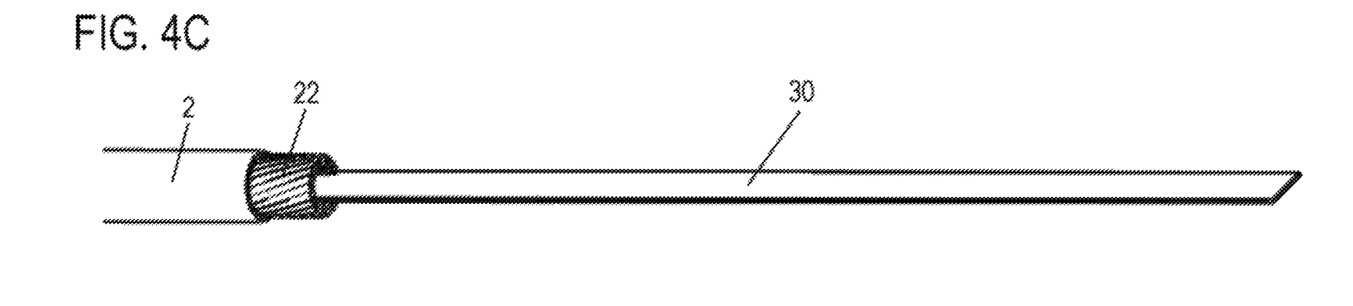

The proximal portion 36 is inserted into the wire mesh 22 of the insertion tube 2 from the distal side. When inserting the flexible plate 30 into the wire mesh 22, the wider distal portion 35 can be used as a stop up to which the flexible plate 30 is inserted into the wire mesh 22. The length of the flexible plate 30 protruding from the wire mesh 22 is predefined in this way.

The proximal portion 36 may also be welded to or glued into or otherwise fastened to the wire mesh 22. Thus, the distal portion 35 of the flexible plate 30 protrudes from the wire mesh 22 of the insertion tube 2 in the distal direction.

Figure 5:
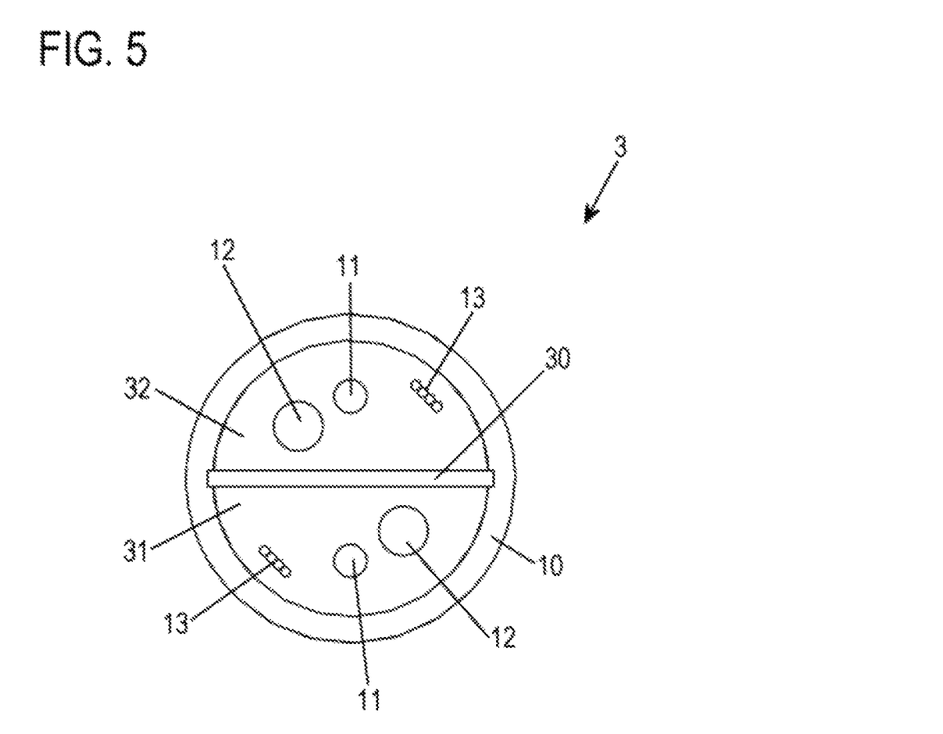
FIG. 5 shows a schematic sectional view across the bending portion of the first embodiment.

The sleeve 10 is drawn over the flexible plate 30. Accordingly, the outer edges of the distal portion 35 press into the elastic inner circumferential surface of the sleeve 10 so that the interior of the sleeve 10 is divided, in cross-section, into a first chamber 31 and a second chamber 32. In other words, the flexible plate 30 divides the interior of the sleeve 10. Each of the first chamber 31 and the second chamber 32 is delimited at the periphery by the inner peripheral surface of the sleeve 10 and the flexible plate 30.

The first chamber 31 and the second chamber 32 extend in the longitudinal direction of the sleeve 10 from the distal end of the insertion tube 2 to the distal end 4. In the embodiment, the distal end of the flexible plate 30 is spaced apart from the proximal surface of the distal end 4, see FIG. 2. Alternatively, the distal end of the flexible plate 30 may abut on the proximal surface of the distal end 4 or be anchored to the distal end 4.

The first chamber 31 and the second chamber 32 are thus separated from each other by the flexible plate 30. Preferably, the first chamber 31 and the second chamber 32 have the same cross-sectional size. Hence, the flexible plate 30 divides the interior of the sleeve 10 into two equal halves. As an alternative, the flexible plate 30 can divide the interior of the sleeve 10 into two unequal halves so that the first chamber 31 and the second chamber 32 then have an unequal cross-sectional size.

In the first chamber 31, a pull rope 11, a camera cable 12 and a light conductor 13 are arranged in the longitudinal direction of the bending portion 3 so that they extend in parallel to the axis of the bending portion 3, see FIG. 5.

The flexible plate 30 is bendable and may be manufactured from spring steel, stainless steel or a bendable plastic material. Despite being bendable, the flexible plate 30 is neither compressible nor expandable. The flexible plate 30 thus has a function similar to that of a spinal column.

Distal End 4

The distal end 4 may act as an endoscope head. In the distal end 4, the pull ropes 11 are anchored. On the distal side of the distal end 4, an optical system (not shown) and a camera (not shown) are disposed. The optical system is connected to the light conductor 13 and ensures illumination of a scenery to be viewed. The camera is connected to the camera cable 12 and takes pictures of the illuminated scenery.

The sleeve 10 may abut on the distal end 4 or, alternatively, cover the outer peripheral side of the distal end 4.

The endoscope 1 according to the invention may be very small. The outer diameter of the insertion tube 2, of the sleeve 10 of the bending portion 3 and of the distal end 4 may be 3 mm or less. In an even smaller design, the outer diameter of the insertion tube 2, of the sleeve 10 of the bending portion 3 and of the distal end 4 may even be 2 or 1 mm or less.

Function of the Invention

By pulling either of the two pull ropes 11 in the proximal direction, the distance between the distal end of the insertion tube 2 and the distal end 4 is reduced. When the pull rope 11 disposed in the first chamber 31 is pulled, the flexible plate 30 is bent toward the side and, therefore, the bending portion 3 pivots to the side of the first chamber 31 (downwards in FIG. 5). When the pull rope 11 disposed in the second chamber 32 is pulled, the flexible plate 30 is bent toward the other side and, therefore, the bending portion 3 pivots to the side of the second chamber 3 (upwards in FIG. 5). Each of the first chamber 31 and the second chamber 32 acts as a pull rope duct for the pull rope 11 arranged in the same.

Advantages of the Invention

The bending portion 3 shows a very simple design, makes use of few components and, therefore, can be manufactured at very low cost.

The bending portion 3 requires no eyelets as a rope guide. This is particularly advantageous for thin insertion tubes, because no cavity must be made available for the eyelets. The separating element 30 provided as flexible plate in the first embodiment divides the interior of the bending portion 3 into the two chambers 31 and 32. Each of the two chambers 31 and 32 serves as rope guide for the respective pull rope 11. Consequently, the pull ropes 11 do not impair each other and nevertheless are safely guided.

Thus, the bending portion 3 according to the invention can be used for an endoscope comprising a very small insertion tube.

Second Embodiment

In the following, a second embodiment of the present invention is described with reference to the FIGS. 6 to 8.

In the second embodiment, in the sleeve 10 of the first embodiment a spring element 18 is arranged. Otherwise, the structure of the second embodiment resembles that of the first embodiment.

Figure 6:
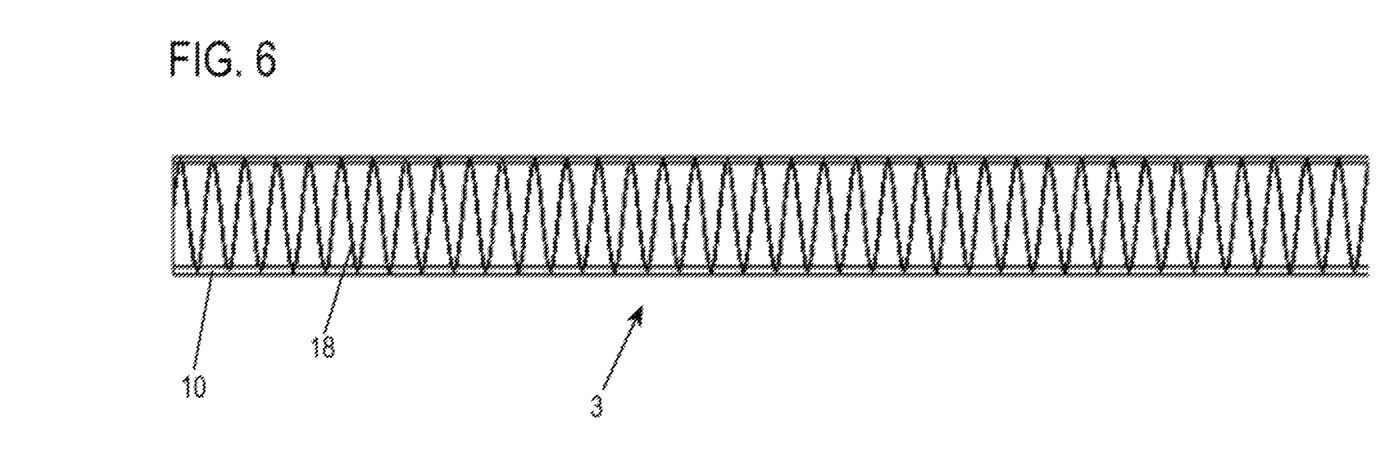
FIG. 6 shows a schematic side view of a sleeve of the bending portion in a second embodiment.

FIG. 6 illustrates a schematic side view of the sleeve 10 of a bending portion 3 of the second embodiment. For reasons of better clarity, the pull ropes 11 and the bendable plate 30 are not shown, nor are the camera cable 12 and the light conductor 13 represented.

Figure 7:
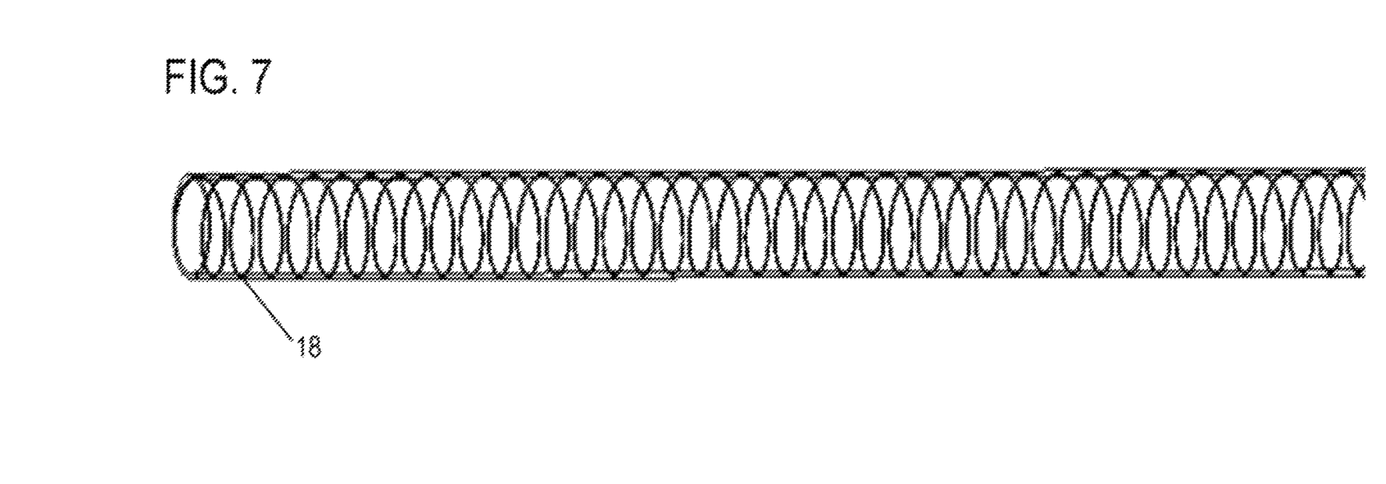
FIG. 7 shows a schematic perspective view of the spring element of the second embodiment.
Figure 8:
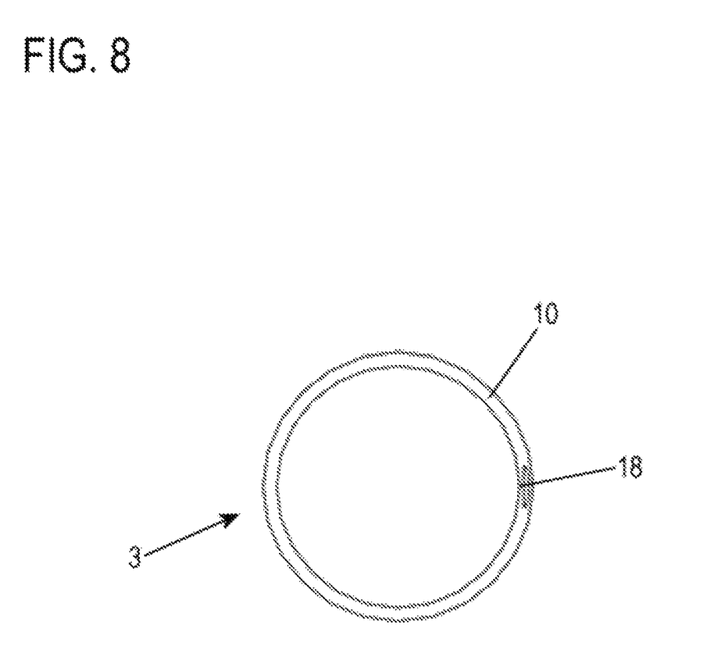
FIG. 8 shows a schematic sectional view across the sleeve of the second embodiment.

In order to impart advantageous bendability to the sleeve 10, a spring element 18 shown in FIG. 7 is embedded in the interior of the sleeve 10. In FIG. 8, the position of the spring element 18 is indicated in the cross-section of the sleeve 10 of the second embodiment.

The sleeve 10 of the second embodiment can be manufactured so that plastic material is injection-molded or extruded onto the spring element 18 such that the spring element 18 is sandwiched between the inner circumferential surface and the outer circumferential surface of the sleeve 10 made from the plastic material.

The sleeve 10 of the second embodiment may thus be configured to be bendable but also stiff and torsion-resistant.

Moreover, the same advantages are resulting as in the first embodiment.

Further Alternatives

In one alternative, a pull rope 11 can be disposed in only one of the two chambers 31, 32. The pull rope in the other chamber of the two chambers 31, 32 is omitted. In this way, a deflecting movement of the bending portion 3 in one direction can be achieved by pulling the one pull rope 11. When the pull rope 11 is relieved, the bending portion 3 adopts its stretched initial position again. In doing so, even more space can be obtained, because the space obtained by the omitted pull rope is available.

In the second embodiment, a spring element 18 is interposed between the inner peripheral surface and the outer peripheral surface of the sleeve 10. In one alternative, a spring element may be disposed on the inner peripheral surface of the sleeve 10 to impart a desired elasticity and bending stiffness to the sleeve 10.

In the first embodiment, the elastic sleeve 10 of the bending portion 3 forms a continuation of the cover 21 of the insertion tube 2 in the distal direction. In one alternative, the elastic sleeve 10 and the cover 21 can be a one-piece cover extending from the control member of the endoscope to the distal end 4.

In the first embodiment, the flexible plate 30 is in the form of an elongate rectangle. The flexible plate 30 may also take other shapes. The cross-section of the bendable plate 30 may take a rectangular, oval, elliptic or race-track shape etc. The race-track shape (or stadium shape) has linear segments inserted between semicircular-type end pieces.

In the embodiments, the separating element is in the form of a flexible or bendable plate. The invention is not limited thereto. The separating element may also be produced as a partition already when the sleeve 10 is manufactured by extrusion, for example. In this case, the separating element is integrally connected to the sleeve 10.

In another alternative, the separating element may be configured as an element cross-shaped in cross-section that divides the interior space of the sleeve 10 into four separate chambers. Further, a separating element dividing the interior space of the sleeve 10 into three or five separate chambers may be provided. Consequently, separating elements that produce any number of chambers in the longitudinal direction of the sleeve 10 can be used. A pull rope can run in each of said chambers. Moreover, when plural chambers separated by a separating element are provided, at least one chamber can be equipped without a pull rope.

In the embodiments, both the optical system including the light conductor 13 and the camera including the camera cable 12 merely constitute examples of use in the endoscope according to the invention and may be modified or even be omitted.

In the embodiments, the separating element can be manufactured from spring steel, stainless steel or a flexible plastic material. In one alternative, the separating element can be made from different materials having different bending properties. Accordingly, the different materials can be arranged in the separating element such that they ensure a preferred bending direction of the separating element. For example, the separating element as a central member can be a bendable metal plate. Said metal plate includes an upper surface and a lower surface and is bendable toward each of the upper and lower surfaces. On the upper surface and/or the lower surface, the metal plate is coated with a different elastic material such as rubber or plastic material. The metal plate is thus bendable toward the respective coating side.

As an alternative, when the invention is applied to a larger endoscope, a working duct, a rinsing duct and/or an ultrasonic sensor etc. can be installed.

The invention can be advantageously applied to a flexible endoscope. The principle of the invention can be applied to any type of endoscope comprising a bending portion.

LIST OF REFERENCE NUMERALS 1 endoscope
2 insertion tube
3 bending portion
4 distal end
10 sleeve
11 pull rope
12 camera cable
13 light conductor
18 spring element
21 cover
22 wire mesh
30 separating element
31 first chamber
32 second chamber
35 distal portion of bendable plate
36 proximal portion of bendable plate

The invention claimed is:

1. An endoscope comprising:
    a flexible insertion tube including:
        an outer cover; and
        an elastic wire mesh positioned beneath the outer cover;
    a bending portion controllable from a proximal side, the bending portion being connected to a distal end of the insertion tube, wherein the bending portion has a sleeve with at least one pull rope extending therein for a pivoting movement of the bending portion, the at least one pull rope being anchored at a distal end of the bending portion; and
    a divider arranged in a longitudinal direction of the sleeve, the divider dividing a cross-section of the sleeve into at least two separate chambers, the divider being anchored at a proximal side thereof to a distal end of the insertion tube, the proximal side of the divider being directly anchored to a distal end of the elastic wire mesh; and
    wherein in one of the at least two chambers separated by the divider, the at least one pull rope is arranged in the longitudinal direction of the sleeve to provide for the pivoting movement of the bending portion.

2. The endoscope according to claim 1, wherein
the at least one pull rope comprises at least two pull ropes, and
a said pull rope of the at least two pull ropes is respectively provided in a said chamber of the at least two chambers separated by the divider, and
the at least two pull ropes are arranged in the longitudinal direction of the sleeve to provide for the pivoting movement of the bending portion.

3. The endoscope according to claim 1, wherein
the divider is arranged within the sleeve so that the divider divides the cross-section of the sleeve into two separated chambers of the same size.

4. The endoscope according to claim 1, wherein
the proximal side of the divider is inserted at the distal end region of the wire mesh.

5. The endoscope according to claim 4, wherein
the divider has a narrower proximal portion inserted into the wire mesh of the insertion tube and a wider distal portion used as a stop up to which the divider is inserted into the wire mesh.

6. The endoscope according to claim 1, wherein
the proximal side of the divider is welded to or glued into the distal end region of the wire mesh.

7. The endoscope according to claim 1, wherein
the sleeve of the bending portion has an outer diameter of 3 mm or less.

8. The endoscope according to claim 1, wherein
the sleeve of the bending portion has an outer diameter of 1 mm or less.

9. The endoscope according to claim 1, wherein
the divider is manufactured from spring steel, stainless steel or any bendable plastic material.

10. The endoscope according to claim 1, wherein
the divider is manufactured from different materials having different flexural properties,
wherein the different materials are arranged in the divider so that they ensure a preferred bending direction of the divider.

11. The endoscope according to claim 1, wherein
the sleeve of the bending portion includes a spring element.

12. The endoscope according to claim 11, wherein
the spring is embedded in the sleeve of the bending portion.

13. The endoscope according to claim 1, wherein
the cross-section of the divider is configured so that the cross-section of the divider is wider in a first direction and is narrower in a second direction being perpendicular to the first direction.

* * * * *